United States Patent
Spilka

(10) Patent No.: US 6,745,445 B2
(45) Date of Patent: Jun. 8, 2004

(54) STENT COMPRESSION METHOD

(75) Inventor: David G. Spilka, Phoenix, AZ (US)

(73) Assignee: Bard Peripheral Vascular, Inc., Tempe, AZ (US)

( * ) Notice: Subject to any disclaimer, the term of this patent is extended or adjusted under 35 U.S.C. 154(b) by 70 days.

(21) Appl. No.: 10/282,485

(22) Filed: Oct. 29, 2002

(65) Prior Publication Data

US 2004/0078953 A1 Apr. 29, 2004

(51) Int. Cl.[7] ............................................. B23P 11/00
(52) U.S. Cl. ..................... 29/407.08; 29/505; 29/515; 29/516; 29/520; 29/234; 29/252; 29/283.5; 623/1.11
(58) Field of Search ..................... 29/407.01, 407.05, 29/407.08, 407.1, 505, 506, 507, 508, 515, 516, 520, 709, 234, 272, 252, 282, 283.5; 623/1.11, 1.23; 606/108, 192, 1, 198, 194

(56) References Cited

U.S. PATENT DOCUMENTS

| | | | |
|---|---|---|---|
| 5,437,083 A | * 8/1995 | Williams et al. | ............... 29/235 |
| 5,738,674 A | 4/1998 | Williams et al. | |
| 5,746,764 A | 5/1998 | Green et al. | |
| 5,810,838 A | 9/1998 | Solar | |
| 5,860,966 A | 1/1999 | Tower | |
| 5,911,452 A | 6/1999 | Yan | |
| 5,944,735 A | 8/1999 | Green et al. | |
| 5,951,540 A | * 9/1999 | Verbeek | ......................... 606/1 |
| 5,971,992 A | 10/1999 | Solar | |
| 5,972,028 A | 10/1999 | Rabenau et al. | |
| 6,009,614 A | 1/2000 | Morales | |
| 6,063,092 A | * 5/2000 | Shin | ......................... 606/108 |
| 6,080,190 A | * 6/2000 | Schwartz | ................... 623/1.22 |
| 6,666,880 B1 | * 12/2003 | Chiu et al. | ................. 623/1.11 |

* cited by examiner

Primary Examiner—David P. Bryant
Assistant Examiner—Jermie E. Cozart
(74) Attorney, Agent, or Firm—Morrison & Foerster LLP

(57) ABSTRACT

A stent compression method for particular use in pre-surgical securing and conforming of a vascular stent upon an angioplasty balloon. One variation of the stent compression method comprises inflating an agioplasty balloon inside a vascular stent in order to secure the vascular stent upon the balloon; applying uniform compression pressure around the balloon/stent unit; and adjusting the internal balloon pressure and the compression pressure so that the balloon/stent unit is compressed. A pressure chamber with an elastic cylindrical membrane mounted inside the chamber may be used to provide the compression pressure. The inflated balloon provides the balancing pressure from inside the stent. The maintenance of internal balloon pressure during the stent compression process may provide uniform distribution of pressure along the stent and even radial compression rate around the circumferential surface of the stent.

28 Claims, 2 Drawing Sheets

STENT COMPRESSION METHOD

FIELD OF THE INVENTION

The present invention relates to surgical angioplasty balloon procedures and more particularly relates to stent compression method for particular use in pre-surgical securement of an angioplasty stent onto a balloon catheter for subsequent implantation of the stent in an angioplasty procedure.

BACKGROUND OF THE INVENTION

A common method of treatment used in restoring blood flow through a diseased segment of a blood vessel is balloon angioplasty. The therapy generally involves the use of a balloon catheter. The balloon catheter is introduced into the cardiovascular system of a patient through the brachial or femoral artery and advanced through the vasculature until the balloon attached to the distal end of the catheter reaches the diseased vessel. The balloon is placed across the diseased vessel segment and is inflated with sufficient pressure to cause the deposit on the intravascular surface to compress against the vessel wall. The balloon is then deflated to a small profile, so that the balloon catheter may be withdrawn from the patient's vasculature and the blood flow resumed through the dilated artery. As should be appreciated by those skilled in the art, while the above-described procedure is typical, it is not the only method used in angioplasty.

Angioplasty of an artery to correct flow obstruction in the vessel may stimulate excess tissue proliferation which then blocks (restenosis) the newly reopened vessel. The physician would usually need perform a second angioplasty procedure. Alternatively, a more drastic procedure, such as a surgical bypass operation may be required to repair or strength the vessel. To reduce the likelihood of restenosis and to strengthen the diseased vessel segment, an intravascular stent may be implanted within the segment of the diseased vessel to maintain vascular patency. The stent is typically transported through the patient's vasculature where it has a small delivery diameter, and then is expanded to a larger diameter, often by the balloon portion of the catheter.

Stents are tubular structures, which are radially expandable to hold a narrowed blood vessel in an open configuration. While stents are most often used to "prop open" blood vessels, they can also be used to reinforce collapsed or narrowed tubular structures in the respiratory system, the reproductive system, biliary ducts or any other tubular body structure.

Since the catheter and stent will be traveling through the patient's vasculature, and in many cases through the coronary arteries, the stent must have a small, delivery diameter and must be attached to the catheter until the physician is ready to implant it. Thus, the stent must be positioned on the balloon catheter such that it does not interfere with delivery, and it must not slip off of the catheter before it reaches the desired location for deployment.

In conventional procedures where the stent is placed over the balloon portion of the catheter, it is necessary to crimp the stent onto the balloon portion to reduce its diameter and to prevent it from sliding off the catheter when the catheter is advanced through a patient's vasculature. Non-uniform crimping can result in sharp edges being formed along the uneven surface of the compressed stent. In addition, non-uniform stent compression may result in a stent/catheter profile that is larger than necessary. Where the stent is not reliably compressed onto the catheter, the stent may slide off the catheter and into the patient's vasculature prematurely as a loose foreign object, which may cause thrombosis. Thus, it is important to ensure the proper compression of a stent onto a catheter in a uniform and reliable manner.

Manual crimping of the stent by hand tends to result in uneven compression due to uneven application of force. Furthermore, it is difficult to determine when a uniform and reliable compression has been achieved. In addition, due to the flexible nature of the stent, some self-expanding stents are difficult to load by hand onto a balloon catheter. Minimizing direct human manipulation may decrease the likelihood of human error, and increase the consistency of the compression procedure. Hence, there is a need for a device for reliably compressing a stent onto a catheter.

There have been mechanisms devised for loading a stent onto a catheter. Examples of such compression devices are disclosed in U.S. Pat. No. 5,911,452, issued Jun. 15, 1999 to Yan, which shows a chamber with flexible tubular diaphragm into which a deflated balloon catheter can be inserted with the stent and the chamber is pressurized to crimp the stent onto the deflated catheter balloon; U.S. Pat. No. 6,009,614, issued Jan. 4, 2000 to Morales, which shows another stent crimping chamber utilizing fluid pressure to crimp the stent onto a deflated catheter balloon; U.S. Pat. No. 5,810,838, issued Sep. 22, 1998 to Soar, which shows further examples of pressurized chambers and collapsible tubular sleeves for compressing stents onto balloon catheters; U.S. Pat. No. 5,971,992, issued Oct. 26, 1999 to Solar, which shows yet another examples of pressurized chamber; U.S. Pat. No. 5,746,764, issued May 5, 1998 to Green et al., which shows further devices for compressing stent onto balloon catheters that include both vacuum and pressurizing fluid pressure means for compression of the stent onto the catheter balloon; U.S. Pat. No. 5,944,735, issued Aug. 31, 1999 to Green et al., which show yet another example of the stent compression device; U.S. Pat. No. 5,972,028 issued Oct. 26, 1999 to Rabenau et al., which shows another variaton of the Green et al. devices supra; U.S. Pat. No. 5,860,966, issued Jan. 19, 1999 to Tower, which shows another version of a stent compression apparatus employing a pressurized diaphragm go compress the stent; each of which is incorporated herein by references in its entirety.

However, the above-cited references do not teach nor suggest inflating the angioplasty balloon prior to compressing of the stent over the balloon. Neither does the above cited references suggest any other means to maintain an internal pressure within the stent to provide a more controlled compression process.

Although the above-described methods by which stents are crimped may be more reliable and constant than manual compression of the stents, these approaches does not overcome problems due to uneven structural collapsing rate of the stent. Stents are mechanical devices that are designed to counter compression pressure when they are expended. However, due to the mechanical nature of the stent, their internal structure is generally not completely homogeneous. The structure of the stent itself could lead to redistribution of pressure within the stent leading to uneven collapse of the stent.

A method that enhances uniform distribution of the compression pressure and at the same time controls the rate contraction of the stent during the compression process may allow even distribution of pressure during the stent compression process and thus, achieve superior placement of the stent over the angioplasty balloon.

SUMMARY OF THE INVENTION

One aspect of the present invention provides for uniform compression of an agioplasty stent over a catheter. In another aspect of the invention, a delivery balloon is inflated inside a stent prior to compressing and securing the stent over the delivery balloon. In yet another aspect of the invention, the stent compression rate, and/or the pressure inside the balloon and the chamber, are carefully controlled during the stent compression process.

One variation of the invention is a method for securing a stent over a balloon on a catheter which comprises the following steps: providing an uncompressed stent; inserting an angioplasty balloon in a deflated state into the stent until the stent is centered upon the balloon; inflating the balloon until the balloon is about the size of the inner diameter of the stent; placing the stent/balloon unit into a compression chamber; applying a positive compression pressure to the outer circumferential surface of the stent; increasing the compression pressure while at the same time decreasing the pressure within the balloon.

In another variation, the deflated balloon with a stent placed around it may be inserted into the compression chamber before the balloon is inflated. The balloon is inflated inside the chamber, followed by the compression process. In yet another variation, the stent may be inserted into the chamber first. After the stent is secured within the chamber, the balloon is inserted within the stent and may then be centered before it is inflated.

In another aspect of the invention, the pressures for compressing the stent and inflating the balloon may be monitored and adjusted with separates valves and/or pressure pumps. In another variation, one or more feed back control mechanisms may be adapted to control the stent compression process. Pressure sensors may be adapted for monitoring the pressure inside the pressure chamber and/or the pressure inside the balloon. In yet another variation, a computer is used for automated control of the stent compression process.

Various pressure sources that are well known to one skilled in the art may be used to provide the pressure for stent compression and for maintaining the balloon in an inflated state. The pressure source includes, but is not limited to, pneumatic pressure and hydraulic pressure.

The balloon and the inflation chamber may be inflated with the same pressure source or alternatively with independent pressure sources. Various pressure pumps that are well known to one skilled in the art may be adapted for providing the inflation pressure needed in the stent compression process.

In one variation, the compression is achieved with hydraulic pressure. Fluids (e.g. water, oil, saline) may be used to inflate a membrane or elastic surface, such that when the membrane or the elastic surface is inflated, it expends inward in a circumferential manner and compresses the object inside the chamber. In another variation, the compression is achieved with pneumatic pressure. Air or gas (e.g. nitrogen, helium, argon, carbon dioxide, or a mixture thereof) may be used to inflate a membrane or elastic surface for compressing the stent. The balloon may also be inflated with fluid (e.g. water, saline), air or gas (e.g., nitrogen, helium, argon, carbon dioxide or a mixture thereof).

With the inner circumferential surface of the stent supported during the compression process, the collapse of the stent will be more controlled and problems associated with non-uniform crimping, such as nicks and kinks along the compressed stent, or sharp edges being formed along the uneven surface of the crimped stent, may be minimized. Furthermore, uniform compression achieved through this process may also minimize dead space between the stent and the angioplasty balloon and a minimal profile for the stent and catheter assembly may thus be achieved.

These and other embodiments, features and advantages of the present invention will become more apparent to those skilled in the art when taken with reference to the following more detailed description of the invention in conjunction with the accompanying drawings.

BRIEF DESCRIPTION OF THE DRAWING

In the accompanying drawings, reference characters refer to the same parts through out the different views. The drawings are intended for illustrating some of the principles of the stent compression methods and are not intended to limit the description in anyway. The drawings are not necessarily to scale, emphasis instead being placed upon illustrating the depicted principles in a clear manner.

DETAILED DESCRIPTION OF THE INVENTION

Before describing the present invention, it is to be understood that unless otherwise indicated this invention is not limited to specific stent, fluids, gases, membranes, or the like, as such may vary. It is also to be understood that the terminology used herein is for the purpose of describing particular aspects of the invention only, and is not intended to be limiting.

A stent is used herein as an example application to illustrate the functionality of the different aspects of the invention disclosed herein. It will be understood that embodiments of the present invention may be applied in a variety of processes and are not limited to compressing a stent over an inflatable device. Variations of the present invention may be adapted for securing other devices or materials over an expandable device for insertion into a hollow body organ inside a mammalian body.

It must also be noted that, as used in this specification and the appended claims, the singular forms "a," "an" and "the" include plural references unless the context clearly dictates otherwise. Thus, for example, the term "a fluid" is intended to mean a single fluid or a mixture of fluids, "a stent" is intended to mean one or more stents, and the like.

Figure 1:
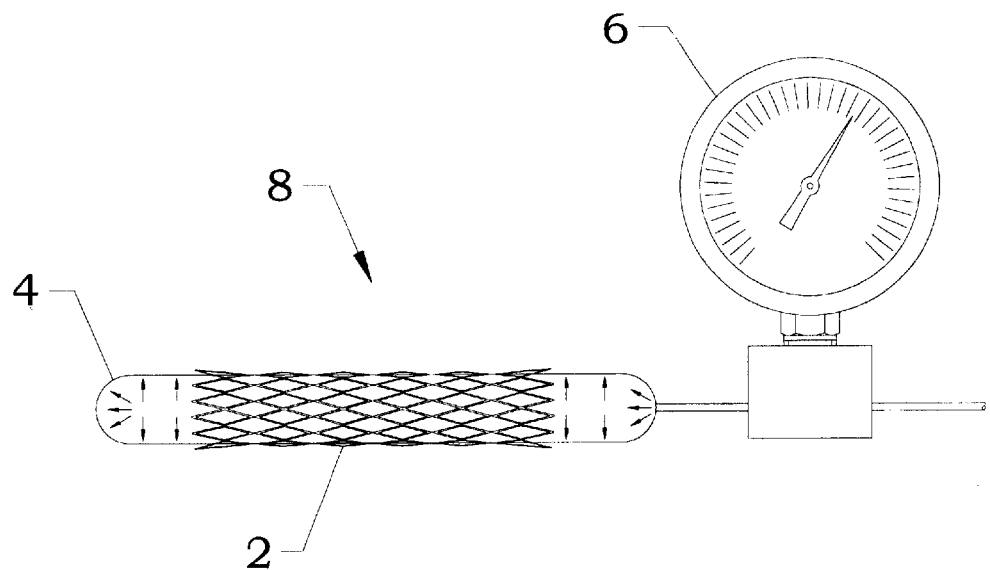
FIG. 1 illustrates an angioplasty balloon inflated inside a stent.

Referring to FIG. 1, a stent device 2 is provided in a non-compressed state. The stent 2 may be at room temperature, or alternatively it may be heated or cooled prior to the compression process. A temperature controlled chamber may be provided to maintain the temperature of the stent 2 at a desirable level during the compression process. In an alternative variation, the environment temperature may be adjusted to assist the compression process.

Stents, stented graphs and other compressible tubular shaped device for deployment in hollow body organs may be compressed with the methods described herein. The stents may be formed of resilient or shape memory material (e.g., spring steel or nitinol) or plastically deformable material (e.g., stainless steel). Examples of stents are set forth in U.S. Pat. No. 4,655,771, issued Apr. 7, 1987 to Wallsten; U.S. Pat. No. 4,954,126, issued Sep. 4, 1990 to Wallsten; U.S. Pat. No. 5,061,275, issued Oct. 29, 1991 to Wallsten, et al.; U.S. Pat. No. 4,580,568, issued Apr. 8, 1986 to Gianturco; U.S. Pat. No. 4,830,003, issued May 16, 1989 to Wolf, et al.; U.S. Pat. No. 5,035,706, issued Jul. 30, 1991 to Gianturco, et al.; U.S. Pat. No. 5,330,400, issued Jul. 19, 1994 to Song; U.S. Pat. No. 5,354,308, issued Oct. 11, 1994 to Simon, et al.; U.S. Pat. No. 5,135,536, issued Aug. 4, 1992 to Hillstead; U.S. Pat. No. 5,161,547, issued Nov. 10, 1992 to Tower; U.S. Pat. No. 5,292,331, issued Mar. 8, 1994 to Boneau; U.S. Pat. No. 5,304,200, issued Apr. 19, 1994 to Spaulding; U.S. Pat. No. 4,733,665, issued Mar. 29, 1988 to Palmaz; U.S. Pat. No. 5,282,823, issued Feb. 1, 1994 to Schwartz, et al.; U.S. Pat. No. 4,776,337, issued Oct. 11, 1988 to Palmaz; U.S. Pat. No. 5,403,341, issued Apr. 4, 1995 to Solar; each of which is incorporated herein by reference in its entirety. The stent compression method may be applied in relation to pressure expandable stents or stented grafts, which are mounted on the balloon of a delivery catheter. The compression method may also be used in relation to self-expanding stents or stented grafts. The self-expanding stents may include a latching mechanism, which engages when the stent or stented graft is radially compressed.

Careful positioning and sound anchoring of the stent or stented graft may be critical to the successful treatment of the underlying medical problem. In this regard, the delivery catheter, which is utilized to insert and position the stent or stented graft, may be an aspect of the overall system. Various types of delivery catheters for stents and stented grafts have been previously known, including those described in U.S. Pat. No. 4,665,918, issued May 19, 1987 to Garza, et al.; U.S. Pat. No. 4,733,665, issued Mar. 29, 1988 to Palmaz; U.S. Pat. No. 4,739,762, issued Apr. 26, 1988 to Palmaz; U.S. Pat. No. 4,762,125, issued Aug. 9, 1988 to Leiman, et al.; U.S. Pat. No. 4,776,337, issued Oct. 11, 1988 to Palmaz; U.S. Pat. No. 4,838,269, issued Jun. 13, 1989 to Robinson, et al.; U.S. Pat. No. 4,994,071, issued Feb. 19, 1991 to MacGregor; U.S. Pat. No. 5,037,427, issued Aug. 6, 1991 to Harada, et al.; U.S. Pat. No. 5,089,005, issued Feb. 18, 1992 to Harada; U.S. Pat. No. 5,102,417, issued Apr. 7, 1992 to Palmaz; U.S. Pat. No. 5,108,416, issued Apr. 28, 1992 to Ryan, et al.; U.S. Pat. No. 5,141,498, issued Aug. 25, 1992 to Christian; U.S. Pat. No. 5,181,920, issued Jan. 26, 1993 to Mueller, et al.; U.S. Pat. No. 5,195,984, issued Mar. 23, 1993 to Schatz; U.S. Pat. No. 5,201,901, issued Apr. 13, 1993 to Harada, et al.; U.S. Pat. No. 5,269,763, issued Dec. 14, 1993 to Boehmer, et al.; U.S. Pat. No. 5,275,622, issued Jan. 4, 1994 to Lazarus, et al.; U.S. Pat. No. 5,290,295, issued Mar. 1, 1994 to Querals, et al.; U.S. Pat. No. 5,306,294, issued Apr. 26, 1994 to Winston, et al.; U.S. Pat. No. 5,318,588, issued Jun. 7, 1994 to Horzewski, et al.; U.S. Pat. No. 5,344,426, issued Sep. 6, 1994 to Lau, et al.; U.S. Pat. No. 5,350,363, issued Sep. 27, 1994 to Goode, et al.; U.S. Pat. No. 5,360,401, issued Nov. 1, 1994 to Turnland; U.S. Pat. No. 5,391,172, issued Feb. 21, 1995 to Williams, et al.; U.S. Pat. No. 5,397,345, issued Mar. 14, 1995 to Lazarus; U.S. Pat. No. 5,405,380, issued Apr. 11, 1995 to Gianotti, et al.; U.S. Pat. No. 5,443,452, issued Aug. 22, 1995 to Hart, et al.; U.S. Pat. No. 5,453,090, issued Sep. 26, 1995 to Martinez, et al.; U.S. Pat. No. 5,456,284, issued Oct. 10, 1995 to Ryan, et al.; and U.S. Pat. No. 5,456,694, issued Oct. 10, 1995 to Marin, et al.

An angioplasty balloon 4 in its deflated state or semi inflated state is inserted into the stent 2, which then may be centered upon the balloon 4 prior to inflation of the balloon 4. Although an angioplasty balloon 4 used in the present example, it is within the contemplation of the present invention that the stent 2 may be placed over other inflatable devices and secured with the method described herein. Thus, the material used for the inflatable device placed within the stent may depend on the configuration of the final product. For example, in one embodiment, the inflatable device may comprise an angioplasty balloon, which is placed within a balloon-expandable stent, such that upon compression of the stent onto the balloon, the balloon/stent unit would be ready for delivery to a patient's vessel. In another embodiment, the inflatable device may comprise a non-adhesive material so that following compression of a self-expanding stent, the inflatable device would be easily removable from within the collapsed stent. In yet another embodiment, a non-adhering coating may be applied to the exterior surface of the inflatable device prior to insertion within the balloon-expandable or self-expanding stent so that following compression of the stent, the inflatable device may be easily removed.

Once the balloon 4 is properly inserted within the stent 2, it is inflated as shown in FIG. 1. The balloon 4 may be inflated to the state where the diameter of the balloon 4 is equal to the inner diameter of the stent 2, as provided in its uncompressed state. Alternatively, the balloon 4 may be inflated until the stent 2 reaches its maximum expanded inner diameter. However, it is not necessary that the stent 2 be expended to its maximum expandable state. It is preferable that the balloon 4 comes into contact with the inner circumferential surface of the stent when it is inflated. Inflating the balloon before placement of the balloon/stent unit 8 inside the compression chamber 10 may prevent the stent 2 from shifting during the placement of the balloon/stent unit 8 inside the compression chamber 10 or during the initial compression by the compression chamber 10.

A pressure gage 6 or pressure sensor may be provided for monitoring the inflation pressure. Alternatively, the volume of air injected into the balloon 4 may be monitored or measured. The pressure source used for inflation of the balloon may be an electronic pressure pump, a mechanical pump, a manual pump, a syringe or other pressure or volume displacement devices that are well known to one skilled in the art. In addition, a electronic controller may be adapted for feed back control of pressure inside the balloon 4 during the inflation process. A fluid (e.g. water, saline, oil), air, or gas (e.g. nitrogen, carbon dioxide, helium, argon) may be used for inflating the balloon.

Figure 2:
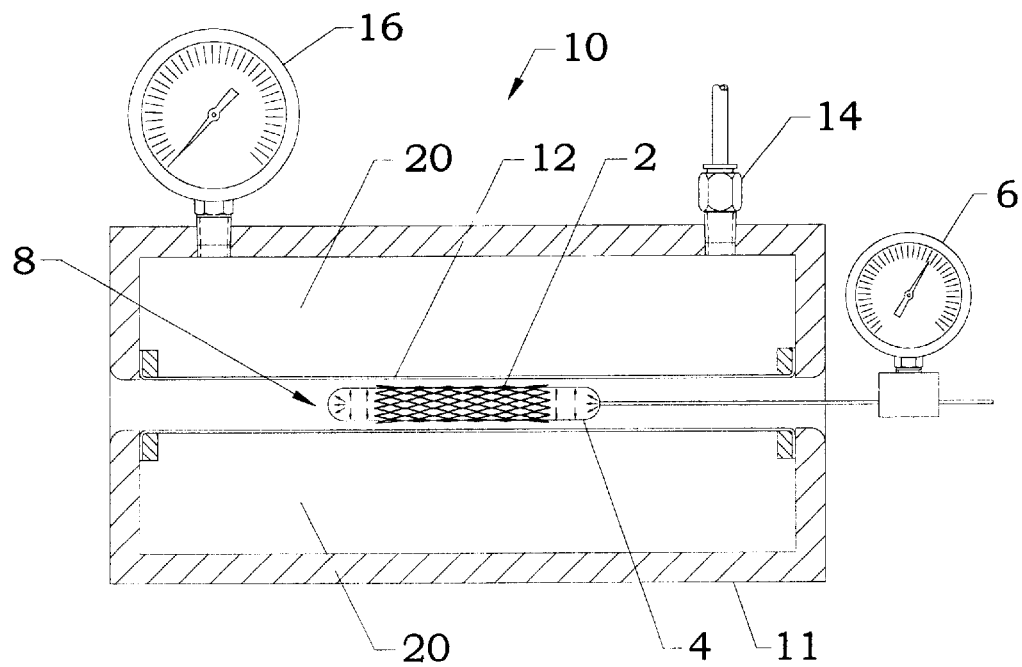
FIG. 2 illustrates a balloon/stent unit being inserted inside a compression chamber.

The inflated balloon/stent unit 8 may then be placed inside a compression chamber 10 as shown in FIG. 2. The compression chamber 10 may be an enclosure or partial enclosure capable of applying inward forces to collapse an object placed inside the enclosure or partial enclosure. The compression chamber 10 may be driven by pneumatic pressure, hydraulic pressure or mechanical pressure. The compression chamber 10 may comprise a housing 11 with a compression layer 12 adapted inside the compression chamber 10 such that the compression layer 12 and the housing 11 form a pressure chamber 20 therebetween, and pressurizing of the pressure chamber 20 will result in the collapse of the compression layer 12. The compression chamber 10 may be similar to any one of those describe in U.S. Pat. No. 5,911,452, issued Jun. 15, 1999 to Yan; U.S. Pat. No. 6,009,614, issued Jan. 4, 2000 to Morales; U.S. Pat. No. 5,810,838, issued Sep. 22, 1998 to Soar; U.S. Pat. No. 5,971,992, issued Oct. 26, 1999 to Solar; U.S. Pat. No. 5,746,764, issued May 5, 1998 to Green et al.; U.S. Pat. No. 5,944,735, issued Aug. 31, 1999 to Green et al.; U.S. Pat. No. 5,972,028 issued Oct. 26, 1999 to Rabenau et al.; and U.S. Pat. No. 5,860,966, issued Jan. 19, 1999 to Tower, each of which is incorporated by reference herein. Preferably the compression chamber 10 is capable of delivering a peak compression pressure between about 200 psi to 500 psi. More preferably, the compression chamber 10 is capable of delivering a peak compression pressure between about 300 psi to 450 psi.

As shown in FIG. 2, in this particular variation, the compression layer 12 comprises an elastic tubing inside the compression chamber 10, within which the balloon/stent unit 8 is situated. However, the compression layer 12 may also comprise an elastic membrane, elastic diaphragm or other mechanically pliable materials. The compression layer 12 may be fabricated from polyethylene (PE), polyethylene terephthalate (PET), nylon or elastomeric materials (e.g., silicone, silicone rubber). The elastic/elastomeric tubing with various durometer hardness/toughness may be selected depending on the mechanical properties and design of the various stents 2 to be compressed. Alternatively, the compression layer 12 may be a tubular diaphragm molded from elastomer capable of withstanding a 450 psi or greater pressure externally applied for transmission of pressure to the stent inserted with the diaphragm lumen during the stent compression process.

In other variations of the present invention, the compression layer 12 may assume various geometries. For example, in the case when the compression layer 12 comprises an elastic tubing, said tubing may be fabricated to have a star-shaped cross-section, or may be fashioned to have beveled ends. At those beveled ends of the elastic tubing, the void created between the beveled surface and the inside walls of the tubular chassis, piston, and end cap, can be filled with a rigid, plastic, fillet insert to help concentrate compression of the elastic tubing. Still other alternative variation of the elastic tubing may have an outside diameter that varies along the length thereof. The elastic tubing may have a dual cone profile, or an ovoid profile. A single cone profile is also contemplated. During the compression process, the particular outside geometry may help concentrate stress at specific regions of the balloon/stent unit 8 when it is positioned within axial space of the tubing.

Similarly, the balloon 4 may be configured in various geometries so that the stent 2, when compressed, conforms to the shape of the balloon 4. In one preferred embodiment, the balloon 4 would have a star-shape cross-section to conform the stent 2 to said star-shape upon collapse thereof. Certainly other geometries are likewise contemplated, depending on the desired final shape of the stent 2. Additionally, the compression layer 12 and balloon 4 could have cooperating geometries to further facilitate the shaping of the stent 2 upon compression thereof. For example, in the case where the compression layer 12 comprises an elastic tubing, both tubing and balloon 4 could take on corresponding shapes (i.e., square, diamond or ribbed) shapes so that upon compression of the stent 2, the shapes of the tubing and balloon 4 would cooperate to conform the stent thereto. Of course, as mentioned above, it may be advantageous to utilize a non-adhesive material for the balloon 4 and/or a non-adhesive coating thereon when desirable to remove the balloon 4 from within the stent 2, following compression thereof.

The compression chamber 10 may have a valve 14, connecting the pressure chamber 20 to a pressure supply source. The pressure source may be an electronic pressure pump, a mechanical pump, a manual pump, a syringe or other pressure or volume displacement devices that are well known to one skilled in the art. In addition, a electronic controller may be adapted for feed back control of pressure inside the pressure chamber 20 during the inflation process. A fluid (e.g. water, saline, oil), air, or gas (e.g. nitrogen, carbon dioxide, helium, argon) may be used for inflating the compression layer 12. Alternatively the pressure supply source may be integrated within the compression chamber 10. In another variation, the compression chamber 10 and the balloon 4 share the same pressure supply source.

The compression chamber 10 may also have a pressure gage 16 or sensor for monitoring the compression pressure. An electronic controller may be adopted for controlling the compression pressure. The electronic controller may be connected to the pressure sensor and the pressure source and capable of feed back control. The electronic controller may further be adapted for monitoring and controlling the pressure inside the balloon 4, in addition to monitoring and controlling the pressure inside the pressure chamber 20, which is located inside the compression chamber 10. The electronic controller may be a computer or a microprocessor based device. By monitoring the pressure inside the pressure chamber 20, $P_C$, and the presser inside the balloon 4, $P_B$, the user or the electronic controller may be able to control the compression pressure and the counterbalance pressure inside the balloon 4 to optimize the compression process. The electronic controller may also be preprogrammed with a protocol for automatic compression of the stent 2 upon the balloon 4.

Figure 3:
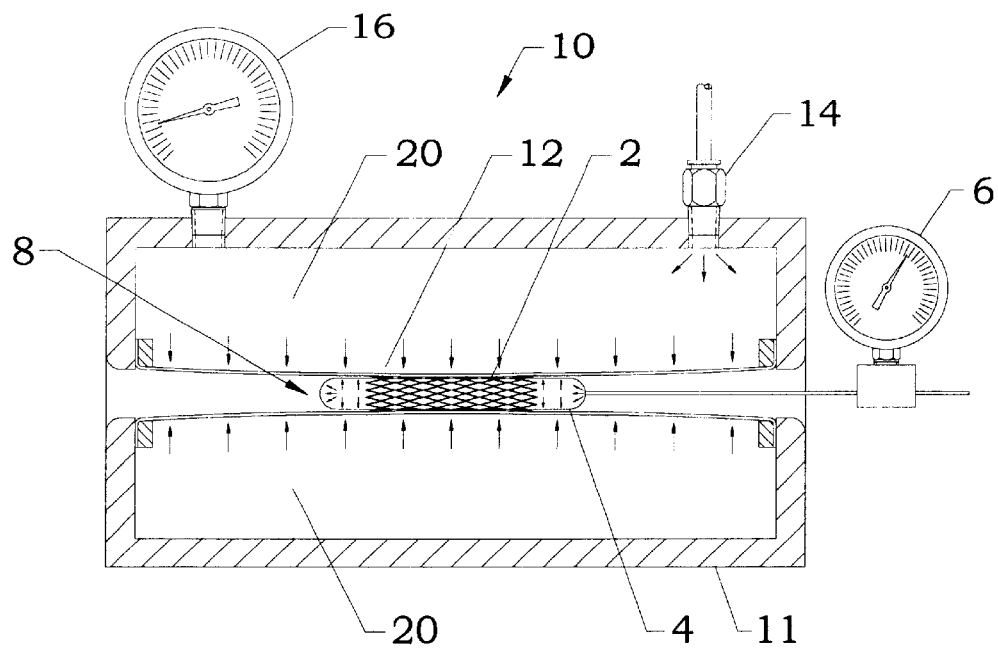
FIG. 3. illustrates pressure inside the pressure chamber being increased, and the compressing layer expand, and comes into contact with the outer circumferential surface of the stent.

A positive pressure may be applied to the pressure chamber inside the compression chamber, forcing the compression layer 12 (i.e. the inner circumferential surface of the elastic tubing, in this variation) to contact the outer circumferential surface of the stent 2, as seen in FIG. 3.

Figure 4:
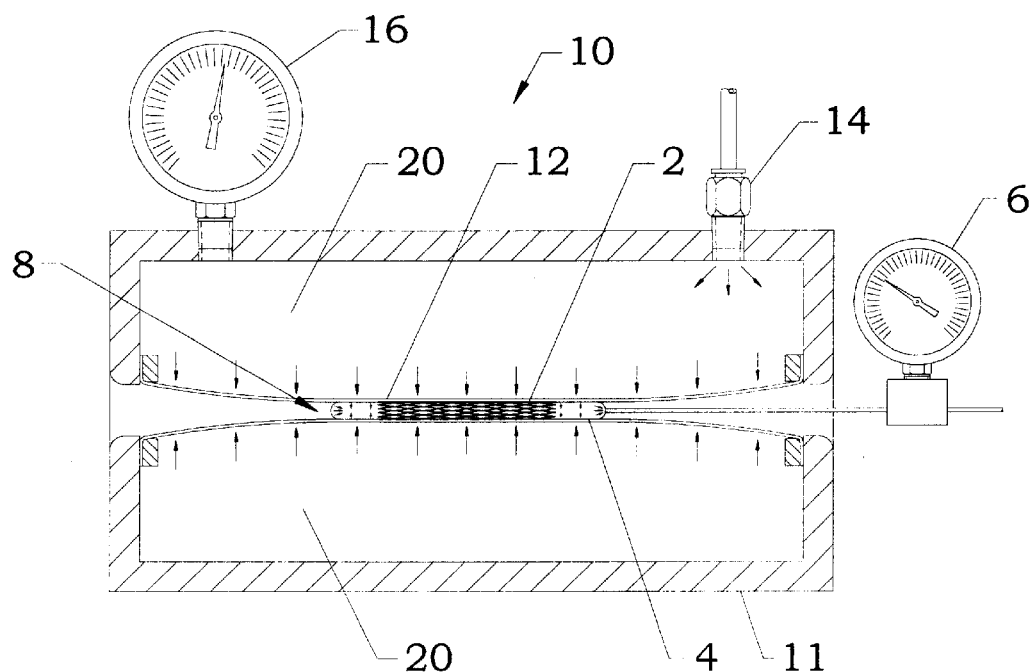
FIG. 4. illustrates the further increase in pressure inside the pressure chamber resulting in the compression of the balloon/stent unit by the compression layer.

Referring now to FIG. 4, a user may continue to increase the pressure inside the pressure chamber 20, $P_C$, while at the same time decreasing the pressure within the balloon 4, $P_B$. Electrically controlled valves or manually controlled valves may be placed between the pressure source and the compression chamber, and between the pressure source and the inner volume of the balloon 4, to allow appropriate modulation of $P_C$ and $P_B$ during the compression process. Valves may also be adapted for releasing pressure inside the pressure chamber and releasing pressure inside the balloon. The appropriate modulation of $P_C$ and $P_B$ during the compression process may allow the stent 2 to compress more uniformly and may remove any unwanted micro-folds on the balloon 4.

When the balloon 4 is deflated and the stent 2 is compressed over the balloon 4, the compression process is complete. An additional step may be added after the balloon is deflated by temporarily applying a negative pressure to the inside of the balloon 4 to further compress the stent 2 over the balloon 4. In another variation, once the balloon 4 is deflated, the pressure chamber is further pressurized to increase the compression pressure on the balloon 4. Once the compression process is completed, the pressure inside the pressure chamber 20 may then be released and the compressed balloon/stent unit 8 may be removed from the compression chamber 10. A physician may deploy the balloon/stent unit 8 inside a patient in a controlled environment with the assistance of appropriate catheter delivery systems that are well known to one skilled in the art.

In another variation, the stent 2 is placed into the compression chamber 10 first, and its position secured by the compression layer 12 (the compression layer may be an elastic membrane or an elastic tube that fits around the stent). Alternatively, the compression layer 12 may be partially inflated so it would fit around the non-compressed stent 2. In another variation, fluid or gas inside the pressure chamber 20 is partially evacuated allowing dilation of the compression layer 12 prior to inserting the stent 2 into said compression layer. Once the stent 2 is secured inside the compression chamber, a deflated balloon 4 or a partially inflated balloon 4 may then be inserted inside the stent 2. The user may center the balloon 4 by adjusting the position of the balloon 4 inside the stent 2. The balloon 4 may then be inflated. The compression process described above may then be followed to compress the stent 2 over the balloon 4.

Another aspect of the invention provides for inflating the compression layer 12 and the balloon 4 with only one pressure source. The balloon 4 may be connected to the pressure source and inflated inside the stent 2. The balloon 4 with the stent 2 may then be placed inside the compression chamber 10. The same pressure source may then be used to supply to the compression chamber 10 to inflate the compression layer 12 inside the compression chamber 10.

In another variation, the balloon 4 is inflated inside the stent 2 first. After the balloon/stent unit 8 is placed inside the compression chamber 10, a positive pressure (which may be supplied by the same pressure source as the one used for inflating the balloon, or alternative it may be supplied by a separate pressure source) is provided to increase the pressure in the pressure chamber 20, $P_C$, to the about same level as the pressure inside the balloon 4 so that $P_C \approx P_B$. $P_C$ is considered as about the same as $P_B$ if the difference in pressure is within 10 psi. Preferably, the pressure difference is within 5 psi. Alternatively, $P_C$ may equal $P_B$. This may be achieved by supplying the pressure to the compression chamber 10 and the balloon 4 with the same pressure source. The pressure inside the balloon is then slowly released, allowing the stent 2 and the balloon 4 to compress.

Alternatively, an auxiliary pressure chamber may be implemented. The auxiliary pressure chamber may be connected to the balloon 4 and the compression chamber 10. While the valves controlling the flow between the auxiliary pressure chamber and the balloon 4, and the valve controlling the flow between the auxiliary pressure chamber and the pressure chamber 20 (which is inside the compression chamber 10) are both closed, the pressure inside the auxiliary pressure chamber, $P^A$, may be increased with a pressure pump. The valve controlling the flow between the auxiliary pressure pump and the balloon 4 may then be opened, thus inflating the balloon and achieving $P_A = P_B$. After the balloon/stent unit 8 is placed inside the chamber, the valve controlling the flow between the auxiliary pressure chamber and the pressure chamber 20 inside the compression chamber may be opened up allowing $P_C = P_A = P_B$, and trapping the stent between the balloon 4, and the compression layer 12.

Once $P_C = P_B$, the pressure inside the balloon may be slowly decreased allowing the compression layer 12 inside the compression chamber 10 to compress the stent/balloon unit 8. This may be achieved by opening a valve and allowing the fluid or gas inside the balloon to escape and at the same time maintaining the pressure inside the pressure chamber 20. The user may control the compression process by controlling the pressure-releasing valve. Once the balloon 4 is deflated, a further compression step may be added by increasing the pressure inside the pressure chamber 20 (which is inside the compression chamber 10). This may be achieved through injecting additional fluid or gas inside the pressure chamber 20 or the auxiliary pressure chamber. A negative pressure may also be applied to the inside of the balloon to facilitate further compression. After the compression process is completed, the pressure inside the pressure chamber 20 is released and the compressed balloon/stent unit 8 may be removed.

In an important aspect of the present invention, the temperature of the compression chamber 10 is maintained at a cool temperature so that the compressed stent remains compressed following chamber depressurization. The temperature of the chamber preferably should be maintained between −45° C. and −15° C., more preferably between −35° C. and −25° C., and most preferably approximately −29° C. during the decompression procedures outlined above to avoid expansion of the stent to its pre-compressed diameter. Obviously, in the case that the stent is loaded into a delivery catheter or other device that maintains the stent's shape, through restraining means or otherwise, while the chamber remains pressurized, the temperature considerations are somewhat alleviated. However, it should also be appreciated that if the stent 2 is made from a shape memory alloy (i.e., Nitinol), temperature considerations may be heightened in particular processing steps.

All publications and patent applications cited in this specification are herein incorporated by reference in their entirety as if each individual publication or patent application were specifically and individually indicated to be incorporated by reference.

This invention has been described and specific examples of the invention have been portrayed. The use of those specifics is not intended to limit the invention in anyway. Additionally, to the extent there are variations of the invention, which are within the spirit of the disclosure or equivalent to the inventions found in the claims, it is our intent that this patent will cover those variations as well.

What is claimed is:

1. A method of compressing a stent on to a balloon comprising the steps of:
    providing a stent;
    inserting a balloon into said stent;
    inflating said balloon;
    placing said balloon, with said stent on the balloon, into a compression chamber; and
    compressing the stent.

2. The method according to claim 1, wherein the inserting step comprises inserting a balloon into said stent wherein said balloon is located on a balloon catheter.

3. The method according to claim 2, wherein the inserting step comprises inserting a balloon into said stent wherein said balloon is located on a balloon catheter and said balloon is deflated.

4. The method according to claim 1, wherein the inserting step comprises inserting a deflated balloon into said stent.

5. The method according to claim 1, wherein the inserting step comprises inserting a partially inflated balloon into said stent.

6. The method according to claim 1, wherein the inserting step further comprises the step of centering said stent on said balloon, such that the stent is located on the center of said balloon.

7. The method according to claim 1, wherein the inflating step comprises inflating said balloon with fluid.

8. The method according to claim 1, wherein the inflating step comprises inflating said balloon until the outer diameter of said balloon is the same as the inner diameter of said stent.

9. The method according to claim 1, wherein the inflating step comprises inflating said balloon until said stent is fully expanded.

10. The method according to claim 1, wherein the compressing step further comprises the steps of:

pressurizing a pressure chamber, said pressure chamber being located within said compression chamber, until a compression layer inside said compression chamber comes into contact with an outer circumferential surface of said stent; and increasing pressure in said compression chamber while decreasing pressure within said balloon.

11. The method according to claim 10, wherein the compressing step further comprises the step of continuing to increase pressure in the pressure chamber after said balloon is deflated.

12. The method according to claim 1, wherein the compressing step further comprises the steps of:

pressurizing a pressure chamber, said pressure chamber being located within said compression chamber, until pressure inside said pressure chamber is approximately equal to the pressure inside said balloon; and releasing the pressure inside said balloon.

13. The method according to claim 12, wherein the compressing step is controlled by an electronic controller.

14. The method according to claim 1, wherein the compressing step further comprises the steps of:

applying a positive pressure in a pressure chamber, said pressure chamber being located within said compression chamber;

forcing a compression layer in the compression chamber to collapse inward toward said stent; and releasing the pressure inside said balloon.

15. The method according to claim 14, further comprising the steps of:

releasing the pressure inside said pressure chamber; and removing the balloon, with the stent on the balloon, from the compression chamber.

16. The method according to claim 1, wherein the compressing step is controlled by an electronic controller.

17. A method for uniformly compressing a vascular stent upon an angioplasty balloon, comprising the steps of:

providing a vascular stent and a deflated balloon, said deflated balloon having a surface;

providing a compression layer within a housing, said compression layer and said housing forming a pressure chamber therebetween;

inserting said deflated balloon into said vascular stent;

inflating said deflated balloon by transmitting pressure into said balloon;

placing said inflated balloon, with the stent positioned around the inflated balloon, into said compression layer;

pressurizing said pressure chamber to compress said compression layer and to apply circumferentially uniform pressure onto said vascular stent to produce compression of the vascular stent into purchase onto the balloon surface by transmitting pressure around said compression layer; and deflating said balloon by releasing pressure inside said balloon.

18. The method according to claim 17, wherein said step of inflating said deflated balloon comprises transmitting fluid pressure into said deflated balloon, and said step of pressurizing said pressure chamber comprises transmitting fluid pressure around said compression layer.

19. The method according to claim 17, wherein the step of inserting said deflated balloon into said vascular stent further comprises the step of centering the stent over said balloon prior to inflating the balloon.

20. The method according to claim 17, wherein prior to said step of placing said inflated balloon, said balloon has an outer diameter equal to an inner diameter of said stent.

21. The method according to claim 17, wherein said step of placing said inflated balloon into said compression layer further comprises the step of dilating said compression layer by at least partially evacuating pressure from said pressure chamber prior to placing said inflated balloon into said compression layer.

22. The method according to claim 17, wherein said compression layer comprises an elastic tubing.

23. The method according to claim 17, wherein said compression layer comprises an elastic diaphragm.

24. The method according to claim 17, wherein said step of pressurizing said pressure chamber further comprises pressurizing said pressure chamber to a point where the pressure inside the pressure chamber is equal to the pressure inside the balloon.

25. A method for uniformly compressing a stent upon an angioplasty balloon, comprising the steps of:

providing a vascular stent and a deflated balloon, said deflated balloon having a surface;

providing an elastic diaphragm within a housing, said elastic diaphragm and said housing forming a pressure chamber therebetween;

inserting said vascular stent and said deflated balloon into said elastic diaphragm such that said vascular stent is positioned around said deflated balloon;

inflating said balloon; and pressurizing said pressure chamber to compress said elastic diaphragm and to apply circumferentially uniform pressure onto said vascular stent to produce compression of the vascular stent into the balloon surface by transmitting pressure around said elastic diaphragm.

26. The method according to claim 25, wherein said step of inflating said deflated balloon comprises transmitting fluid pressure into said deflated balloon, and said step of pressurizing said pressure chamber comprises transmitting fluid pressure around said elastic diaphragm.

27. A method for uniformly compressing a stent upon an angioplasty balloon, comprising the steps of:

providing a stent and a deflated balloon, said deflated balloon having a surface;

providing an elastic diaphragm within a housing, said elastic diaphragm and said housing forming a pressure chamber therebetween;

inserting said stent into said elastic diaphragm such that said diaphragm is positioned around said stent;

inserting said deflated balloon into said stent;

inflating said balloon;

pressurizing said pressure chamber to compress said elastic diaphragm and to apply circumferentially uniform pressure onto said vascular stent to produce compression of the vascular stent on to the balloon surface by transmitting pressure around said elastic diaphragm; and releasing pressure inside said balloon.

28. The method according to claim 27, wherein said step of inserting said stent into said elastic diaphragm further comprises the step of dilating said elastic diaphragm by at least partially evacuating pressure from said pressure chamber prior to inserting said stent into said elastic diaphragm.

* * * * *